United States Patent [19]

Grollimund et al.

[11] Patent Number: 4,832,062
[45] Date of Patent: May 23, 1989

[54] DUAL FLOSSER

[76] Inventors: Everett C. Grollimund, 3306 Nuttree Woods Place,, Midlothian, Va. 23113; William H. Angus, 5600 Promontory Point Rd., Midlothian, Va. 23113

[21] Appl. No.: 145,052

[22] Filed: Jan. 19, 1988

[51] Int. Cl.[4] .............................................. A61C 15/00
[52] U.S. Cl. .................................... 132/327; 132/324
[58] Field of Search ...................... 132/91, 92 R, 92 A

[56] References Cited

U.S. PATENT DOCUMENTS

| 1,518,021 | 12/1924 | Truxicco | 132/91 |
| 3,853,134 | 12/1974 | McCord | 132/92 A |
| 3,927,686 | 12/1975 | Zambito | 132/91 |
| 4,005,722 | 2/1977 | Bragg | 132/92 R |
| 4,041,962 | 8/1977 | Johansson et al. | 132/91 |
| 4,655,233 | 4/1987 | Laughlin | 132/91 |

FOREIGN PATENT DOCUMENTS

| 2923057 | 12/1980 | Fed. Rep. of Germany | 132/91 |
| 635201 | 12/1927 | France | 132/91 |

*Primary Examiner*—Paul J. Hirsch
*Attorney, Agent, or Firm*—John F. C. Glenn

[57] ABSTRACT

Flosser holds two threads side-by-side for insertion between a pair of teeth and draws the threads laterally apart to bend partially around the teeth while flossing them.

15 Claims, 6 Drawing Sheets

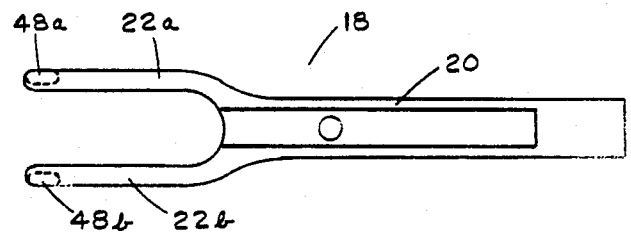
FIG. 6
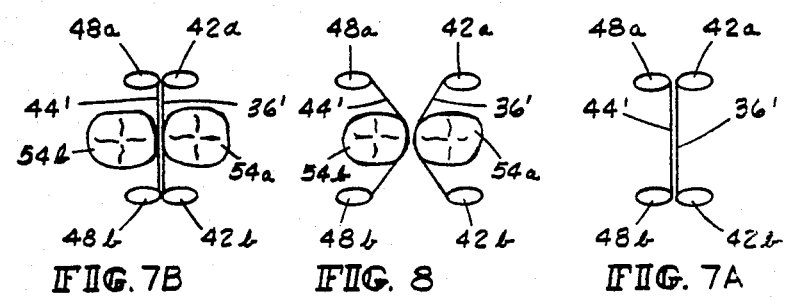
FIG. 7B   FIG. 8   FIG. 7A
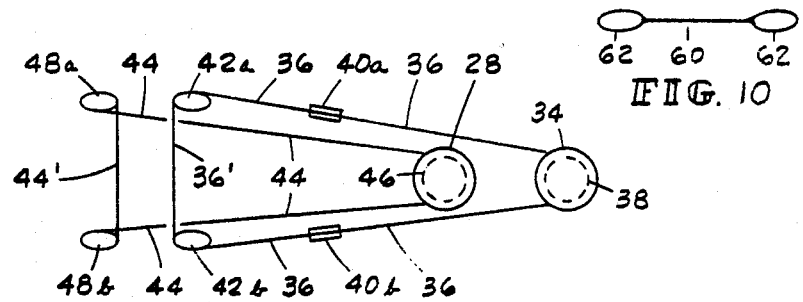
FIG. 9
FIG. 10

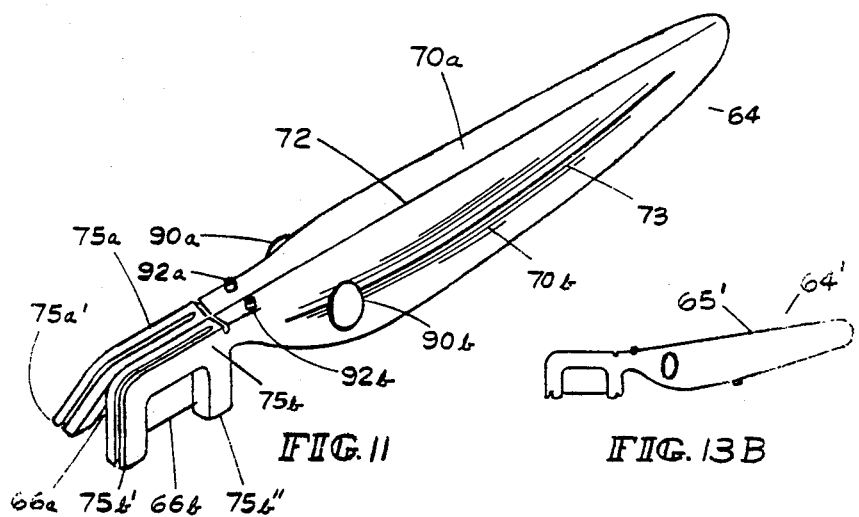
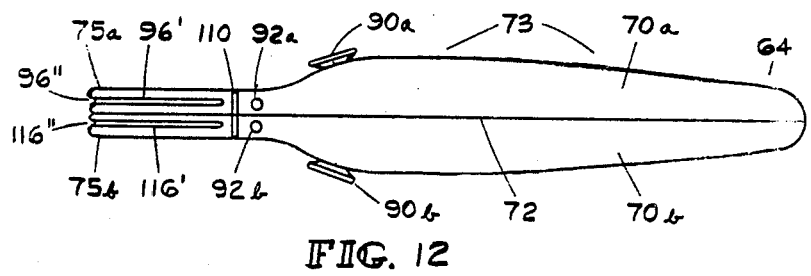
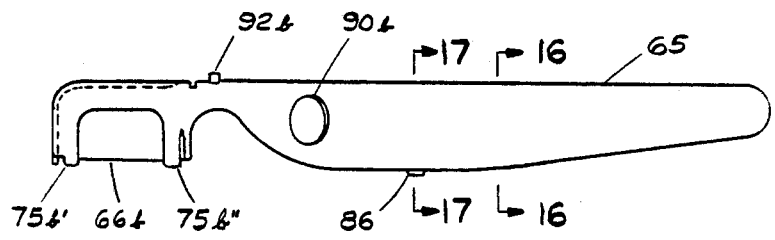

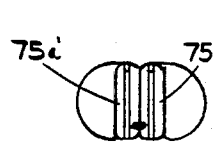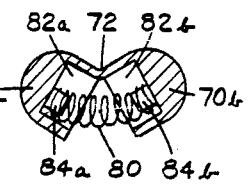
FIG. 14  FIG. 15  FIG. 16
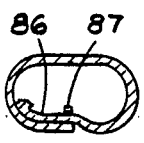 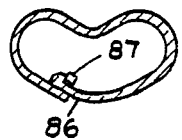
FIG. 17  FIG. 18
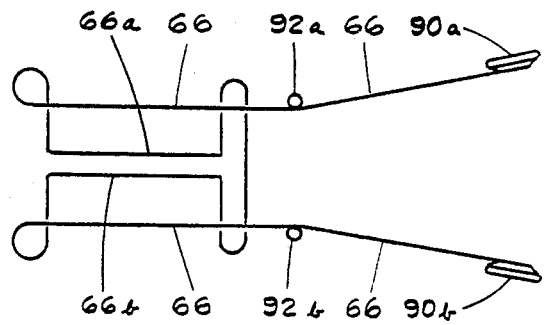
FIG. 24

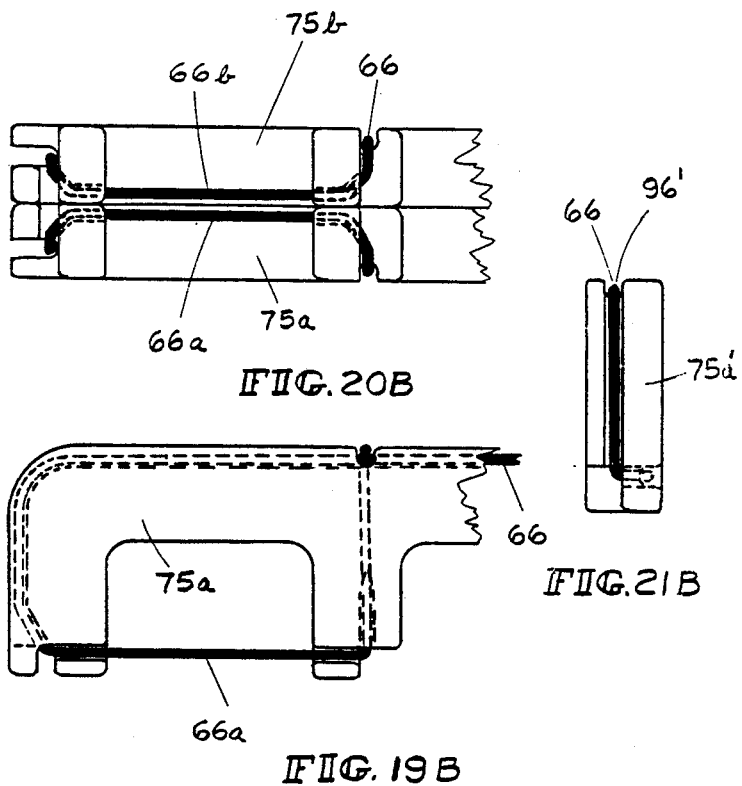

DUAL FLOSSER

BACKGROUND OF THE INVENTION

Then flossing thread is used for cleaning between adjacent teeth a single strand is usually held in tension between the fingers of a person whose teeth are being cleaned, or else between a pair of spaced mechanical elements projecting from a common supporting handle. In either case, the common practice is to insert a single strand between the adjacent teeth and to rub it up and down against the adjacent side of one tooth while pulling in one direction against that side, and hhereafter against the adjacent side of the other tooth while pulling in the opposite direction against the other side.

SUMMARY OF THE INVENTION

In accordance with the present invention, two side-by-side lengths of flossing thread are inserted between a pair of adjacent teeth and then drawn apart so that one length bends around one of the teeth and the other length bends around the other tooth. While in that condition the two lengths of thread are then rubbed up and down against the adjacent teeth, so that the opposite sides of the two teeth are thoroughly and simultaneously cleaned.

For this purpose the two lengths of thread are held between different pairs of prongs at the ends of a pair of forks carried by a common handle. The forks are mounted on the handle in a manner permitting relative movement of the forks in one direction to bring the two lengths of thread into substantially side-by-side relation for entry between adjacent teeth, and then in the reverse direction to move the two lengths laterally apart so that they are parallel until bent oppositely by the teeth. To accomplish this the forks may be overlapped and made movable in a direction lengthwise of each other and transverse to the direction of the threads while they are parallel. In another and present preferred arrangement, the forks may be hinged together for swinging movement between a position in which the threads are together and a flossing position in which the threads are apart.

Other objects, advantages and features of the invention will become apparent as the following more detailed disclosure proceeds.

BRIEF DESCRIPTION OF DRAWINGS

Present preferred embodiments of the invention are shown in the accompanying drawings, which show, for purposes of illustration only the following figures:

FIG. 6 shows a top plan view of a fork component of the flosser shown in FIGS. 1 and 2;

FIG. 7A shows a pair of flossing threads and two sets of thread holding means at te left end of the flosser shown in FIGS. 1 and 2;

FIG. 7B shows a pair of human teeth with the threads of FIG. 7A inserted therebetween;

FIG. 8 corrresponds to FIG. 7B but shows the threads against the teeth after moving apart the two sets of thread holding means;

FIG. 9 shows diagramatically how the threads of FIG. 7A are extended to two sets of anchoring means on the flosser shown in FIGS. 1 and 2;

FIG. 10 shows an alternate form of flossing thread for use in the flosser shown in FIGS. 1 and 2 (or in the second species of flosser shown in the following Figures);

FIG. 11 shows an isometric perspective view of a second species of flosser embodying the invention, in which a pair of thread lengths for flossing are mounted to extend in the direction of the length of the flosser (but omitting the thread elsewhere);

FIG. 12 shows a top plan view of the flosser shown in FIG. 11;

FIG. 13A shows a side view of the flosser shown in FIG. 11;

FIG. 13B shows a view corresponding to FIG. 13A but showing a modification of the apparatus in which the length of the handle is at an acute angle to the lengths of the thread held for flossing;

FIG. 14 shows an end view of the flosser shown in FIG. 11, viewed from the left side of FIG. 12;

FIG. 15 corresponds to FIG. 14 but shows two components of the flosser pivoted about an axis extending lengthwise of the flosser;

FIG. 16 shows a section on the line XVI—XVI in FIG. 13, but after pivoting to the position shown in FIG. 15;

FIG. 17 shows a section on the line XVII—XVII in FIG. 13 while the components are pivoted together as shown in FIGS. 11-14;

FIG. 18 corresponds to FIG. 17 but shows the components while pivoted apart;

FIG. 19B corresponds to FIG. 19A but shows the thread;

FIG. 20B corresponds to FIG. 20A but shows the thread;

FIG. 21B corresponds to FIG. 21A but shows the thread;

FIG. 24 shwws diagrammatically the path of a single length of thread from one end anchored on one side of the flosser shown in FIG. 11 et seq. to its tther end anchored on the other side of the flosser.

DETAILED DESCRIPTION OF PRESENT PREFERRED EMBODIMENTS 0F THE INVENTION

Figure 1:
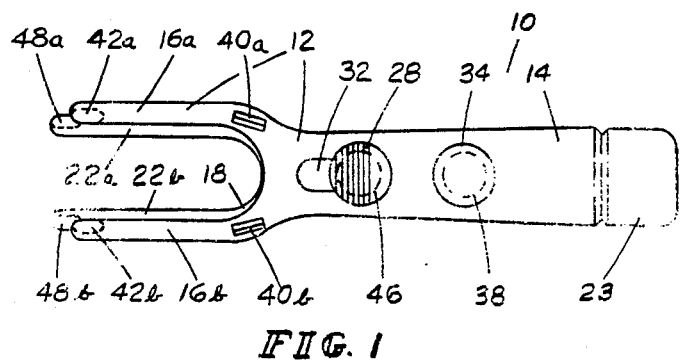
FIG. 1 shows a top plan view of a dental flosser embodying the invention.

Referring now more particularly to the drawings, and initially to FIGS. 1-6, a dental flossing instrument 10 has a fixed fork 12 having an elongated handle 14 terminating at its forward end in a pair of integral spaced prongs 16a and 16b. Handle 14 serves as handle for the whole instrument as well as for fork 12. The instrument also has a movable fork 18 having an elongated portion 20 terminating at its forward end in a pair of integral spaced prongs 22a and 22b. A flexible cap 23 covers the rear end of handle 14 and a tongue 20' at the end of handle portion 20.

The portion 20 of movable fork 18 fits within and is slidable along a channel 24 extending along most of the length of handle 14. The two forks 12 and 18 are thus movable lengthwise relative to each other. A cylindrically coiled compression spring 26 is mounted in the rear of channel 24 between its end wall formed in handle 14 and a rear wall 20" of movable handle portion 20. Spring 26 resiliantly urges the movable fork 18 forward so that the projecting ends of its prongs 22a and -b are resiliently urged away from the projecting ends of prongs 16a and -b.

A control and anchoring knob 28 has an integral stem 30 secured to movable fork portion 20 and extending through a slot 32 along the top of handle 14. Knob 28 extends beyond stem 30 to overlie and slide against the top surface of handle 14 on opposite sides of slot 32. When knob 28 and stem 30 slide along slot 32, fork portion 20 slides along channel 24. During this sliding movement tongue 20' also moves but continues to cover spring 26.

An anchoring knob 34 is secured in a fixed position on top of handle 14 for holding the ends of a length of flossing thread 36 while an intermediate portion of the thread extends between prongs 16a and -b. One end of thread 36 is pinched and thereby anchored in a groove 38 around knob 34. The thread is then lead through a fixed guide 40a on top of handle 14 to and around a small projection 42a at the end of prong 16a, thence to and around a like projection 42b at the end of prong 16b, through a like guide 40b (on the other side of the top of handle 14 from guide 40a), and finally back to knob 34, where the other end of the thread is similarly anchored in pinching groove 38.

One end of a second length of a flossing thread 44 is similarly anchored in a pinching groove 46 around knob 28. Then the thread 44 is led to and around a projection 48a on the end of prong 22a, thence to and around a projection 48b on the end of prong 22b, and finally back to knob 28, where the other end of thread 44 is anchored in groove 46.

The threads 36 and 44 are mounted as described with an initial tension in the portions 36' and 44' of threads 36 and 44 between the respective pairs of prong projections 42a and -b and 48a and -b. The said pairs are brought close together to position thread portions 36' and 44' in close side-by-side parallel relation, as shown in FIG. 7A. The instrument 10 is then held by hand and guided to bring said thread portions between a pair of teeth 54a and 54b, as shown in FIG. 7B.

Figure 2:
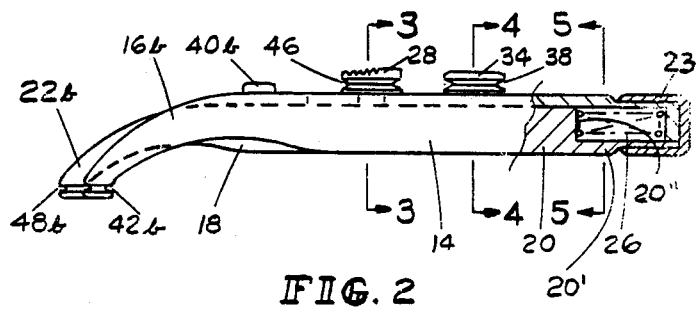
FIG. 2 shows a side view partially sectioned, of the flosser shown in FIG. 1.
Figures 3, 4, 5:
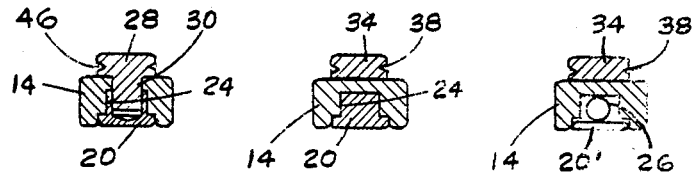
FIG. 3 shows a section taken on the line III—III in FIG. 2.
FIG. 4 shows a section taken on the line IV—IV in FIG. 2.
FIG. 5 shows a section taken on the line V—V in FIG. 2.
Figure 20A:
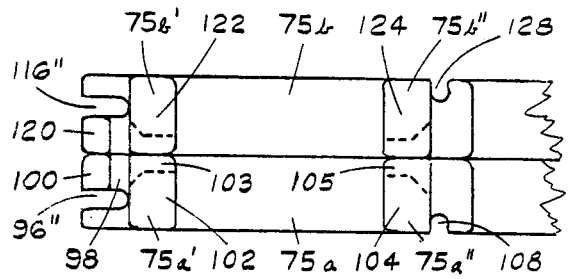
FIG. 20A shows a bottom plan view of what is shown in FIG. 19A.
Figure 21A:
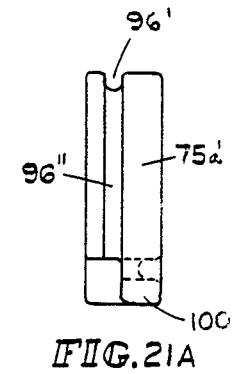
FIG. 21A shows an end view of the left end of what is shown in FIG. 19.
Figure 19A:
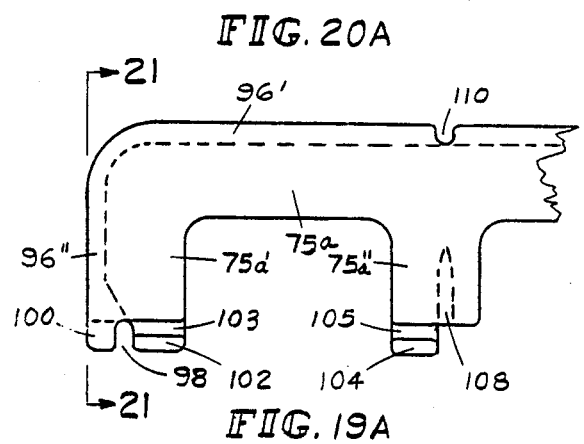
FIG. 19A shows an enlarged broken-away view of the left end of FIG. 13, omitting the thread entirely.

Spring 26 presses handle portion 20 forward (to the left as shown in FIGS. 1 and 2). This spring pressure may be augmented or offset by pressure in one direction or the other exerted by thumb or finger against knob 28, in order to control thread tension, especially during flossing. The resultant pressure on handle portion 20 moves the pair of projections 48a and -b away from projections 42a and -b as knob 28 moves forward along slot 32 to the same extent. The initial tension in thread portions 36' and 44' is not affected by this forward movement until the separating movement between the two pairs of projections 42a and -b and 48a and -b causes thread portions 36' and 44' to bend around the respective teeth 54a and -b, as shown in FIG. 8. This thread bending requires further resilient inward bending of prongs 16a and -b and 22a and -b, thus adding tension in thread portions 36' and 44' between teeth 54a and -b. The tension thss added may be modified by thumb or finger on knob 28 to achieve the amount of tension desired during flossing. The forward end of instrument 10 is then moved up and down enough to rub threads 36' and 44' up nnd down along adjacent sides of teeth 54a and -b This simultaneous rubbing action of the two threads against both of the teeth effects an efficient flossing action between the teeth. When that is completed, the operator of the instrument uses a thumb or finger to slide knob 28 rearward against spring 26 until projections 42a and -b and 48a and -b are again close together. The threads are then withdrawn from between the pair of teeth just flossed and may be inserted between a pair of unflossed teeth, after which knob 28 is released by the operator to permit spring 26 to move prongs 22a and -b forward again, so that the operation can be repeated between the second pair of teeth. This may be repeated between successive adjacent teeth until all teeth are flossed. The instrument may then be rethreaded and put away until used again.

Instead of anchoring the ends of threads 36 and 44 in knobs 28 and 34, these threads may be replaced by a corresponding number of short lengths of thread 60 (FIG. 10) each having a loop 62 at its opposite ends adapted to be slipped over one of the prong projections 42a or -b or 48a or-b. These short lengths are selected to be.just short enough to provide a slight tension when the prongs are released from the inward pressure needed to position them for mounting a pair of the loops over one of the pair of projections 42a and -b, or 48a and -b.

The above-described flosser 10 shown in FIGS. 1–10 holds the tooth-contacting theead portions 36' and 44' so that they extend transversely to the length of the handle 14, and are moveable relative to each other in a direction perpendicular to their lengths. In the modified forms of flosser 64 shown in FIGS. 11, 12 and 13A and 64' shown in FIG. 13B the corresponding thread portions 66a and 66b extend parallel (FIG. 13A) or nearly parallel (FIG. 13B) to the length of its handle (shown at 65 in FIG. 13A and 65' in FIG. 13B), an are moveable relative to each other in a direction transverse to the length of the handle. For this purpose a divergence from parallel of up to about 15° is satisfactory.

The flosser 64 has a pair of side-by-side elongated oody portions 70a and 70b hinged together for pivotal movement about an axis extending in the direction of the elongation. Instead of having hinges in the form of separate units, the two body portions are preferably molded as a unit with an integral connecting web 72 capable of flexing to provide the said pivotal movement. Nylon and other flexible polymers may be used as the molding material for the body.

The middle and rear ends of body portions 70a and -b provide the handle 73 of flosser 64. The active end of the flosser is at its other end, where forward projections 75a and 75b extend integrally from body portions 70a and -b.

Figures 22A, 22B, 23:
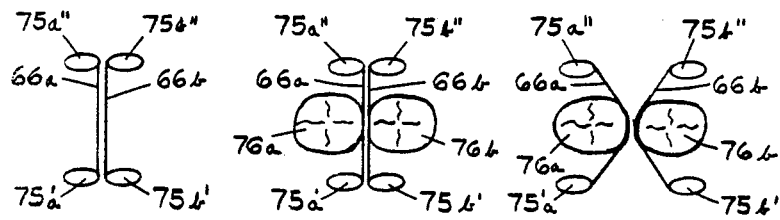
FIG. 22A shows a pair of lengths of flossing thread held by two sets of thread holding means at the left end of the flosser shown in FIGS. 11-21.
FIG. 22B shows a pair of human teeth with the threads shown in FIG. 22A therebetween.
FIG. 23 corresponds to FIG. 22B but shows the threads against the teeth after moving apart the two sets of thread holding means.

Projection 75a has a pair of spaced arms 75a' and -a" carrying thread portion 66a, and projection 75b has a pair of spaced arms 75b' and 75b" carrying thread portion 66b. Both sets of these spaced arms project away from the pivot axis along which web 72 bends. Pivoting body portions 70a and 70b together brings thread portions 66a and 66b close together parallel in side-by-side relation (FIG. 22A). Thread portions 66a and -b may then be inserted between a pair of teeth 76a and 76b (FIG. 22B), and then swung apart until they bend partially around the teeth (FIG. 23) preliminary to moving them up and down to floss the teeth.

A compression spring 80 biases body portion 70a and -b to pivot apart. The spring is mounted in opposed cavities 82a and 82b in handle portions 70a and -b. Integral studs 84a and 84b project inside handle portions 70a and -b to anchor the ends of the spring. The body portions are thus normally pivoted open, subject to limiting action of a latch 86 and catch 87 (FIGS. 17 and 18)

The body portions are initially held together by the hand of the operator around the handle while positioning thread portions 66a and -b between the pair of teeth 76a and -b (FIG. 22B). The hand then relaxes to permit the spring to pivot the two pairs of thread carrying arms apart until the thread is resiliently pressed by the spring action against the teeth (FIG. 23). The strength of the spring is therefore selected to provide the desired flossing pressure against the teeth. When ready to withdraw the threads from the teeth, the hand preferably tightens on the handle to bring the two sets of arss and thread portions together while overcoming the spring resistance, and the threads are then withdrawn from the teeth.

To thread the flosser shown in FIGS. 11, 12 and 13A (or 13B), and 19A and-B, a single long thread 66 is anchored at one end on a knob 90a on the side of body portion 70a, then drawn past a post 92a on body portion 70a, along a groove 96' on the top of projection 75a, along a continuing groove 96" down the outer side of the arm 75a', then drawn along a groove 98 between spaced projections 100 and 102 at the end of arm 75a', around one corner of projection 102, along a groove 103 in the side of projection 102 facing arm 75b', across the gap between arms 75a' and -a" (the flossing length of thread 66a shown in FIG. 11), along a groove 105 in the side facing arm 75b" of a projection 104 at the end of arm 75a", around one corner of projection 104, across the side of projection 104 facing the handle end of the flosser, along an upwardly extending relief 108 indented into the side of arm 75a" facing away from arm 75b", and along a groove 110 across the top of arm 75a".

The grooves and projections of the two sets of arms 75a' and -a" and 75b' and b", and posts 92a and -b and knobs 90a and -b on body portions 70a and -b are mirror images of each other. Accordingly, the path of thread 66 continues from groove 110 across the pivot axis in a reverse course along arms 75b" and -b' to reach post 92b and knob 90b. More particularly, the thread passes along a relief 128 on arm 75b" (corresponding to relief 108), - around a projection 124 on arm 75b" (corresponding to projection 104), across the gap between arms 75b" and 75b' (the flossing length o thread 66 shown in FIGS. 11 and 13A), around a corner of a projection 122 from arm 75b' (corresponding to projection 102), between projection 122 and a projection 120 on arm 75b' (correspnnding to projection 100), up a groove 116" on arm 75b' and along a groove 116' on projection 75b (corresponding oo grooves 96" and 96'), past post 92b and onto knob 90b, where it is secured.

Thread 66 is pulled to desired tightness against knobs 90a and -b and secured there preliminary to flossing. When fresh lengths of thread between arms 75a' and -a" and between arms 75b' and -b", thread 66 may be detached from knobs 90a and -b, pulled toward one knob and thereby drawn away from the other until the said fresh lengths have appeared, and then secured to one knob, tightened, and secured to the other knob.

Instead of using thread 66 as described above it may be replaced by a pair of looped threads like the thread 60 shown in FIG. 10, one with its end loops slipped over projections 102 and 104 and into grooves 103 and 105, and the other with its end loops slipped over projections 122 and 124 and their corresponding grooves, oollowing an installation procedure in each case like that desrribed above in connection with thread 60.

While present preferred practices and embodiments of the invention have been illustrated and described, it will be understood that the invention is not limited thereto, but may be otherwise variously embodied and practiced within the scope of the following claims.

We claim:

1. Apparatus for flossing between teeth, comprising a first pair of spaced means adapted to hold a first length of flossing thread therebetween, a second pair of spaced means adppted to hold another length of flossing thread therebetween, and means to support said first and second pairs of menas and to permit movement of them between a first position in which they are adapted to hold a pair of flossing thread lengths substantially side-by-side suitbly for insertion between a pair of teeth, and a second position suitable for use after insertion between a pair of teeth and in which said pair of thread lengths are urged apart suitably for them to bend partially around and floss simultaneously against the adjacent sides of the pair of teeth.

2. Apparatus according to claim 1, comprising resilient means urging said first and second pairs of means to move from said first position to said second position.

3. Apparatus according to claim 2, comprising manually operable means for urging said first and second pairs of thread holding means to move from said second position to said first position with sufficient force to override the opposing action of said resilient means.

4. Apparatus according to claim 1, in which the means to support and permit movement comprises a pair of side-by-side elongated members adapted to move relative to each other, one of said members being connected to said first pair of thread holding means and the other said member being connected to said second pair of thread holding means.

5. Apparatus according to claim 4, in which one of said elongated members is adapted to be held by hand during use of the apparatus in flossing, and the other said elongated members is mounted for movement lengthwise of said one elongated member, whereby the thread held by one pair of spaced holding means moves laterally relative to the other pair of thread holding means during said lenghhwise movement of one of the elongated means relative to the other, and whereby threads held by the two pairs of spaced thread holding means extend generally transverse to the length of said hand holdable member.

6. Apparatus according to claim 4, in which the means connecting the elongated members functions as a hinge to cause swinging movement of the llongated members relative to each other about an axis extending parallel to their directions of elongation.

7. Apparatus according to claim 6, in which said pairs of thread holding means are each adapted to hold the thread therebetween at least approximately parallel to said hinge axis, within a range of divergence from parallel of about 15 dggrees.

8. Apparatus according to claim 6, in which said pairs of thread holding means are each adapted to hold the thread therebetween extending in a line substantially convergentoon an extension of said hinge axis away from said elongated members.

9. Apparatus according to claim 6, in which the elongate members and the hinge means holding them togeheher are asingle integral plastic molding.

10. Apparatus according to claim 6, comprising means mounted outside of each of said elongated members and adapted to detachably attach thread, and thread guiding means on the outside of each of said elongated members and of each of the pairs of spaced thread holding means, said attaching and guiding means being adapted to permit one end of a thread to be attached to one of said attaching means, and permitting the thread so attached to be extended from there down to the extremity of one of said thread holding means of said first pair of thread holding means, across the space between that means and the extremity of the other thread holding means of said first pair, up to and over the top of an extension of the hinge axis of the elongated members and out to the extremity of one of the thread holding means of said second pair of thread holding means, across the gap to the extremity of the other thread holding means of said second pair of thread holding means, back up from said last mentioned extremity and thence to the other attaching means.

11. Apparatus according to claim 10, including a thread so monnted on the apparatus.

12. Apparatus according to claim 10, in which said extremities each have a post around part of which thread may be guided and supported, said post having a groove along at least a portion of said part of the post, said groove being adapted to oppose thread against the post being pulled laterally away from the post.

13. Apparatus according to claim 12, comprising thread so mounted in the apparatus.

14. Apparatus according to claim 10, in which the elongated members and the hinge means holding them together are a single integral plastic molding.

15. Apparatus according to claim 1, including a pair of flossing threads each having a loop at each of its eds, one of said threads having the loops at its ends secured to said first pair of spaced means, and the other of said threads having the loops at its ends secured to said second pair of spaced means.

* * * * *